(12) United States Patent
von Segesser

(10) Patent No.: US 6,626,859 B2
(45) Date of Patent: Sep. 30, 2003

(54) HIGH PERFORMANCE CANNULAS

(75) Inventor: Ludwig K. von Segesser, Lausanne (CH)

(73) Assignee: Coraflo Ltd., Lausanne (CH)

( * ) Notice: Subject to any disclaimer, the term of this patent is extended or adjusted under 35 U.S.C. 154(b) by 0 days.

(21) Appl. No.: 09/764,006

(22) Filed: Jan. 17, 2001

(65) Prior Publication Data

US 2002/0010440 A1 Jan. 24, 2002

Related U.S. Application Data

(60) Provisional application No. 60/176,688, filed on Jan. 18, 2000.

(51) Int. Cl.$^7$ ............................................. A61M 25/00
(52) U.S. Cl. ........................... 604/28; 604/43; 604/524; 604/525; 604/526; 604/530
(58) Field of Search .................... 604/28, 43, 523, 604/524, 525, 526, 527, 530

(56) References Cited

U.S. PATENT DOCUMENTS

| | | | |
|---|---|---|---|
| 5,067,491 A | * 11/1991 | Taylor, II et al. | ....... 600/486 X |
| 5,573,509 A | * 11/1996 | Thornton | ................ 604/524 X |
| 5,674,240 A | 10/1997 | Bonutti et al. | |
| 5,795,289 A | 8/1998 | Wyttenbach | |
| 5,817,071 A | 10/1998 | Dewindt et al. | |
| 5,827,319 A | 10/1998 | Carlson et al. | |
| 5,911,702 A | 6/1999 | Romley et al. | |
| 5,976,114 A | 11/1999 | Jonkman et al. | |
| 6,036,711 A | 3/2000 | Mozdzierz et al. | |
| 6,072,154 A | 6/2000 | Maynard | |
| 6,096,012 A | 8/2000 | Bogert et al. | |
| 6,102,894 A | 8/2000 | Dysarz | |

FOREIGN PATENT DOCUMENTS

| | | |
|---|---|---|
| EP | 0 839 549 A1 | 5/1998 |
| WO | WO 99/15226 | 4/1999 |

OTHER PUBLICATIONS

International Search Report issued Jun. 26, 2001, PCT/IB01/00191.

* cited by examiner

Primary Examiner—Gregory Huson
Assistant Examiner—Kathleen J. Prunner
(74) Attorney, Agent, or Firm—Mintz Levin Cohn Ferris Glovsky and Popeo PC

(57) ABSTRACT

A cannula having a proximal end, a distal end, and a lumen extending between the proximal and distal ends is provided. The diameter of the lumen of the cannula can be varied to take into account differences in the diameter of access and target vessels during cannulation. The cannula is further characterized by at least one mechanism that, upon actuation, serves to alter the conformation of the cannula between a normal profile conformation and a low profile conformation. The normal profile conformation is characterized by the cannula having a lumen diameter at the point of insertion which is smaller than the lumen diameter both proximal and distal to the point of insertion, with the lumen diameter distal to the point of insertion also expandable to the diameter of the cannulized vessel of the patient. The low profile conformation is characterized by the cannula having a lumen diameter at the point of insertion that is greater than the lumen diameter distal to the point of insertion.

15 Claims, 9 Drawing Sheets

HIGH PERFORMANCE CANNULAS

RELATED APPLICATIONS

This application claims priority to U.S. Ser. No. 60/176,688, filed Jan. 18, 2000, which is herein incorporated by reference.

FIELD OF THE INVENTION

The invention relates to cannulas and, more particularly, to high performance cannulas, where the diameter of the lumen of the cannula can be varied.

BACKGROUND OF THE INVENTION

Cannulas are used in a wide variety of applications. For example, cannula assemblies are typically used in minimally invasive surgical procedures such as laparoscopic, endoscopic, and arthroscopic procedures. Cannulas can be used to deploy operating instrumentation during such minimally invasive procedures. Additionally, during coronary surgery, venous and arterial cannulas are used to conduct blood between the body and the bypass equipment. Moreover, cannulas are also used as vents, sumps, and for chest tube fluid suction. Cannulas are also used in a variety of non-medical contexts.

SUMMARY OF THE INVENTION

In one aspect, this invention involves a cannula having a cannula body with a proximal end, a distal end, and a lumen extending between the two ends. The cannula is made of a flexible material that can be altered to allow the diameter of the lumen to be varied. Upon termination of the alteration, the diameter of the lumen is returned to its normal profile conformation. The cannula according to the invention can be inserted into an object in need of cannulization.

In some embodiments, the cannula also includes one or more mechanisms that allow the diameter of the lumen to be altered. Suitable mechanisms may include coils; springs; extensible, compressible, or releasable wings; foils; folds; and/or cages. Upon release of the mechanism(s), the cannula will either return to its normal profile conformation or expand to the diameter of the surrounding vessel or environment.

In other embodiments, the diameter of the lumen at the point of insertion is narrower than the diameter at the proximal and distal ends. The diameter at the proximal and distal ends of the cannula can either be the same or different. In other embodiments, the diameter at the distal end is greater than the diameter at the point of insertion.

In still other embodiments, the proximal end of the cannula is coated with a water-tight coating, such as a plastic.

The cannulas according to the invention are characterized by a high flow rate of fluids through the cannula. For example, the flow rate of fluids though the cannula may range between 100 mL/min and 6 L/min.

In another aspect, the invention involves a cannula having a cannula body, a distal end, a proximal end, and a lumen with a variable diameter extending between the proximal and distal ends. In one embodiment, the cannula has a narrow diameter at the point of insertion, and, in another embodiment, the diameter of the lumen distal to the point of insertion expands to be the same as the diameter of the lumen proximal to the point of insertion. In a further embodiment, the diameter of the lumen distal to the point of insertion is greater than the diameter of the lumen at the point of insertion. In yet another embodiment, the lumen diameter distal to the point of insertion is expandable to the diameter of a vessel of the patient. In a further embodiment, the proximal end of the cannula is coated with a water-tight coating, such as a plastic.

In yet another aspect, the invention involves a cannula having a cannula body, a distal end, a proximal end, a lumen with a variable diameter extending between the proximal and distal ends, as well as one or more mechanisms that allow the diameter of the lumen to be altered. In various embodiments, the mechanism(s) may include coils; springs; extensible, compressible, or releasable wings; foils; folds; and/or cages. In one embodiment, the cannula will return to its normal profile conformation upon release of the mechanism. In another embodiment, the cannula will expand to the diameter of the surrounding vessel or environment upon release of the mechanism.

In another embodiment, the diameter of the lumen at the point of insertion is narrower than the diameter of the lumen at the proximal and distal ends of the cannula. The diameter of the lumen at the proximal and distal ends may be the same or different. Additionally, the diameter of the lumen at the distal end can be greater than the diameter at the point of insertion.

In a further embodiment, the proximal end of the cannula is coated with a water-tight coating, such as a plastic.

In a further aspect, the invention provides methods of using the cannulas of the invention. In one embodiment, the invention involves the steps of placing the cannula in its low profile conformation, inserting the cannula, and returning the cannula to its normal profile confirmation and allowing the cannula to expand distal to the point of insertion. In another embodiment, the invention involves the steps of activating one or more of the cannula's diameter varying mechanism(s), inserting the cannula, and deactivating the mechanism(s), thereby allowing the cannula to expand distal to the point of insertion. In this embodiment, the mechanism(s) can be coils; springs; extensible, compressible, or releasable wings; foils; folds; and/or cages.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the following detailed description and from the claims.

DETAILED DESCRIPTION OF THE INVENTION

High Performance Cannulas

Figure 1A:
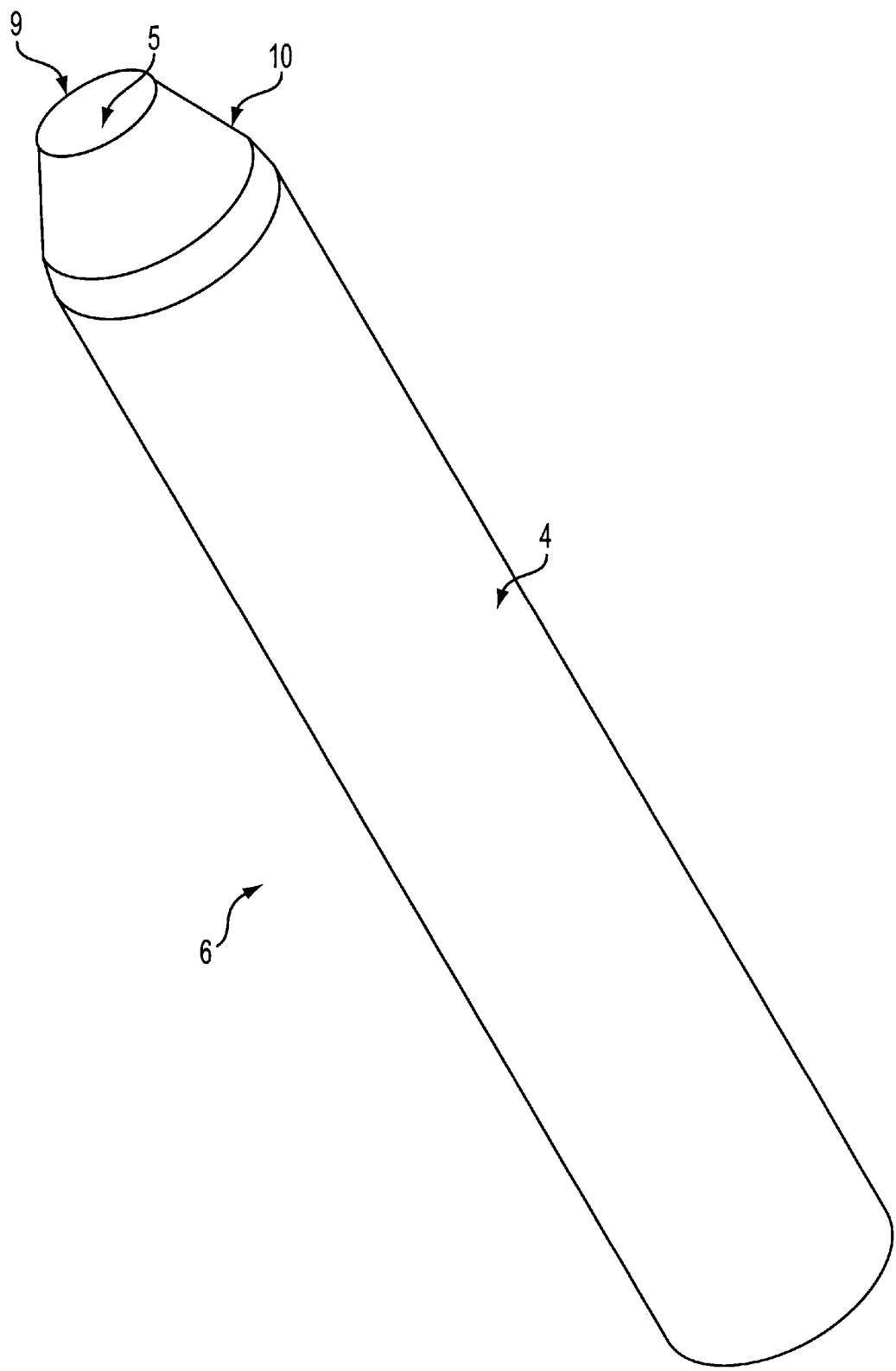
FIG. 1A is a computer-generated drawing showing a cannula according to the present invention in its normal profile conformation.
Figure 1B:
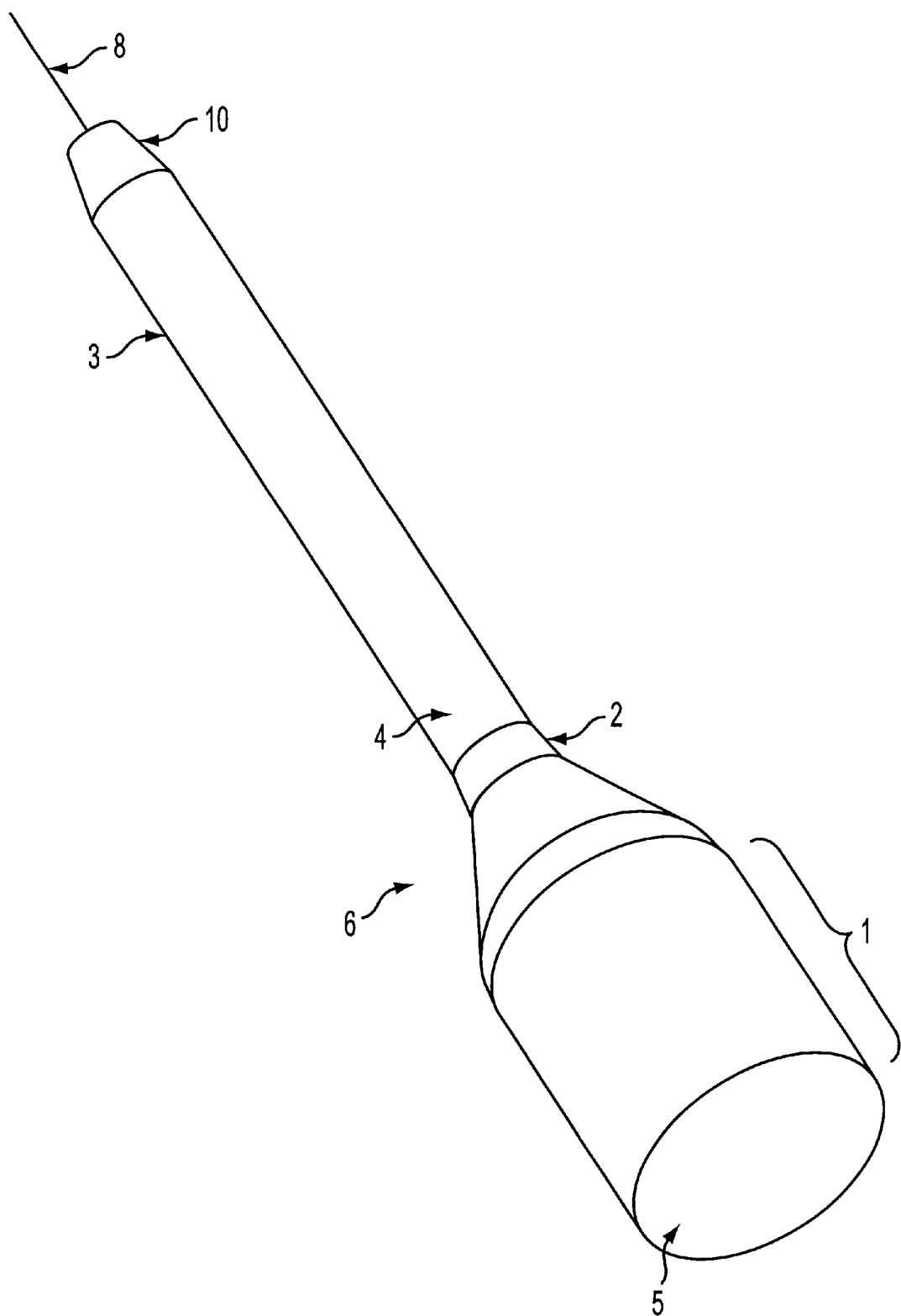
FIG. 1B is a computer-generated drawing showing a cannula according to the present invention in its low profile conformation.

Minimally invasive open heart surgery presents new problems and challenges, some of which are due to inadequate cannula design. Presently, the external diameter of cannulas to be used in target blood vessels is determined by the internal diameter of the access vessel, which is usually smaller than that of the target vessel. For example, in peripheral cannulation, the diameter of the access vessel (e.g. the femoral vein) is significantly smaller than the diameter of the target vessel (e.g. the vena cava). As a result of this difference in diameters, relatively high cannula gradients can occur. Therefore, during peripheral cannulation, venous return is poor and must be augmented with vacuums or pumps. During minimally invasive open heart surgery, the tip of the venous cannulas cannot be placed in the right atrium of the heart, which is open by definition. Thus, it can be impossible to reach target flow rates despite this augmentation of the venous return, because the floppy caval veins collapse and obstruct the orifices of the cannula.

A person of ordinary skill will recognize that a short segment of a tube or vessel with a narrow internal diameter will not impede flow through the tube or vessel. Specifically, the segment of narrow internal diameter may constitute between 0% and 50% of the total length of the object. The skilled artisan will also recognize that, in a clinical setting, coronary artery stenoses of less than 50% of the diameter of the artery are not considered significant, and, thus, are not operated on. By "coronary artery stenoses" is meant any stricture or narrowing of a coronary artery. In contrast, a long portion of a tube or vessel with a small or narrow diameter will impede flow through the object.

Based on these principles and observations, a cannula having a narrow diameter only where absolutely necessary would be expected to have much better flow rate characteristics than one having a narrow diameter over most of its length. Thus, the cannulas according to the present invention may have a small diameter only at the point of insertion. By "point of insertion" is meant the location where the cannula is inserted into the object to be cannulized. Examples of point of insertion include, but are not limited to, arterial walls, venous walls, and the skin. Preferably, the narrow diameter of the cannula occurs over less than 50% of the total length of the cannula, more preferably, less than 40%, more preferably less than 30%, more preferably less than 20%, and most preferably, less than 10%.

Because of the narrow diameter of the cannula at the point of insertion, the access aperture will be small. By "access aperture" is meant the hole that allows the cannula to access the object or vessel to be cannulized.

Those skilled in the relevant arts will recognize that cannulation is not limited to medical contexts. For example, non-medical uses for the high performance cannulas of the invention include, but are not limited to, any situation where a continuous fluid flow and a small access aperture is desired. Examples of non-medical uses of the high performance cannulas according to the invention include, but are not limited to, methods for repairing ruptured pipe, hose, or tubing where a continuous fluid flow and a small access aperture are needed without having to replace the entire length of ruptured pipe, hose, or tubing.

Likewise, the cannulas according to the invention can be used as previously described in the art. For example, see U.S. Pat. Nos. 6,102,894; 6,096,012; 6,072,154; 6,036,711; 5,976,114; and 5,817,071, each of which is incorporated herein by reference.

When used in a medical context, the cannulas according to this invention can take advantage of the geometry of an individual's vascular tree. Specifically, cannulas according to this invention are able to compensate for the differences in diameter between access vessels (typically smaller in diameter) and target vessels (typically larger in diameter). To compensate for these differences in diameter, the diameter of the lumen of the high performance cannula is adjustable before, during and after cannulation (i.e., insertion). Specifically, after cannulation the diameter of the cannula either expands to that of the surrounding vessel or environment or returns to its normal profile conformation.

Turning now to the drawings, and to FIGS. 1–4 in particular, an embodiment of the cannula 6 according to the invention is shown. This embodiment of the cannula 6 comprises a cannula body 4 having a proximal end 1, a distal end 3, and a lumen 5 having an internal diameter that extends between the proximal end 1 and the distal end 3.

By "proximal" is meant the external end of the cannula 6 that is not inserted into the object or vessel to be cannulized. Similarly, by "distal" is meant the end of the cannula 6 that is inserted into the object or vessel to be cannulized.

In one embodiment, the cannula 6 is made of a flexible, deformable, moldable, etc. material that can be altered to allow the diameter of the lumen 5 to be varied. By "diameter of the lumen" is meant the diameter of the lumen 5 of the cannula body 4.

In another embodiment, the cannula 6 may also comprise one or more means for altering the conformation of the cannula or mechanisms that allow the diameter of the lumen 5 to be varied. Such mechanisms may, for example, be coils; springs; extensible, compressible, or releasable wings; foils; folds; and/or cages. One skilled in the art will recognize that other suitable mechanisms may also be employed. In one embodiment, the cannula comprises at least one mechanism that upon actuation serves to alter the cannula between a normal profile conformation and a low profile conformation. For example, the mechanism, when activated, serves to place the cannula 6 in its low profile confirmation, thereby decreasing the diameter of the lumen 5. Upon release of the mechanism, the cannula 6 either returns to its normal profile conformation or expands to the diameter of the surrounding vessel or environment. In an alternate embodiment, the activated mechanism(s) maintains the cannula 6 in its normal profile conformation. In this embodiment, upon release of the mechanism, the cannula 6 is placed in its stretched conformation, thereby decreasing the diameter of the lumen 5.

Figure 2A:
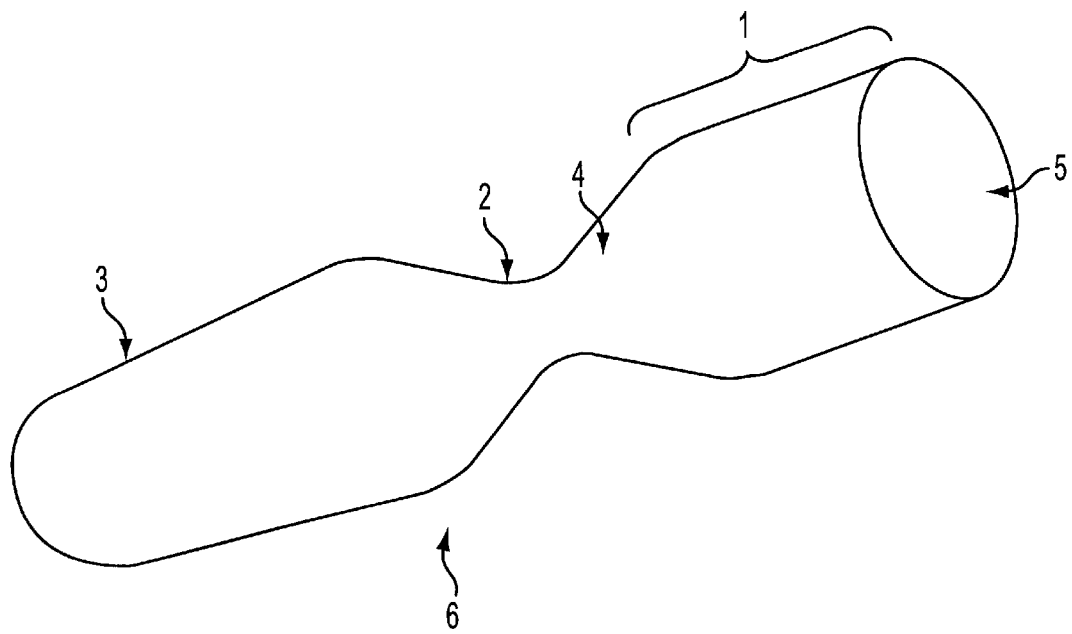
FIG. 2A is a perspective view showing a cannula according to the present invention in a normal profile conformation.
Figure 2B:
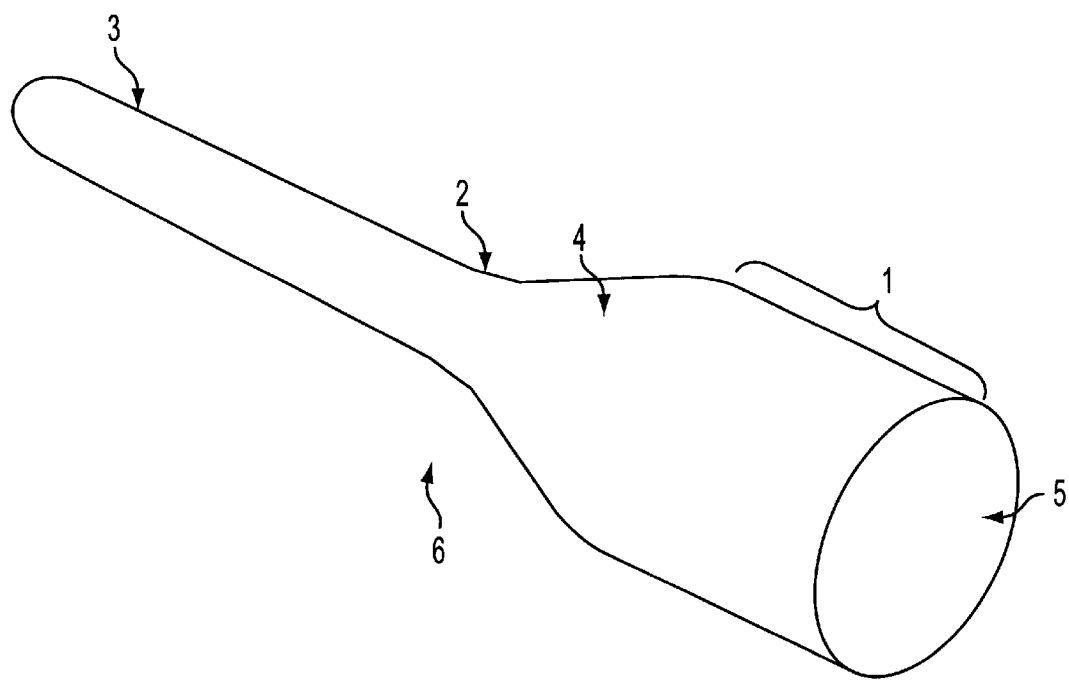
FIG. 2B is a perspective view showing a cannula according to the present invention in a low profile conformation.
Figure 3A:
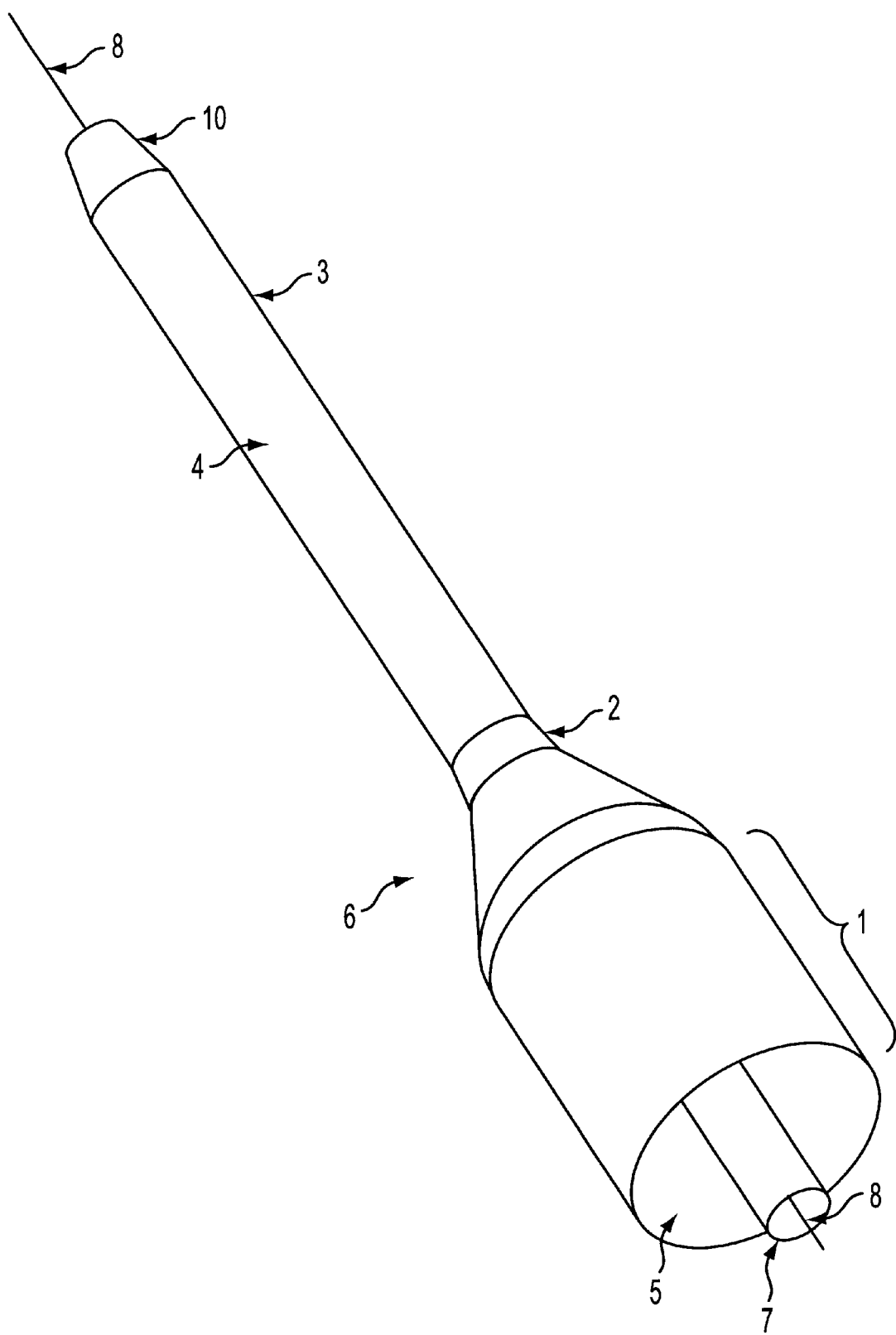
FIG. 3A is a computer-generated drawing showing the high performance cannula according to the invention stretched on a mandrel.
Figure 3B:
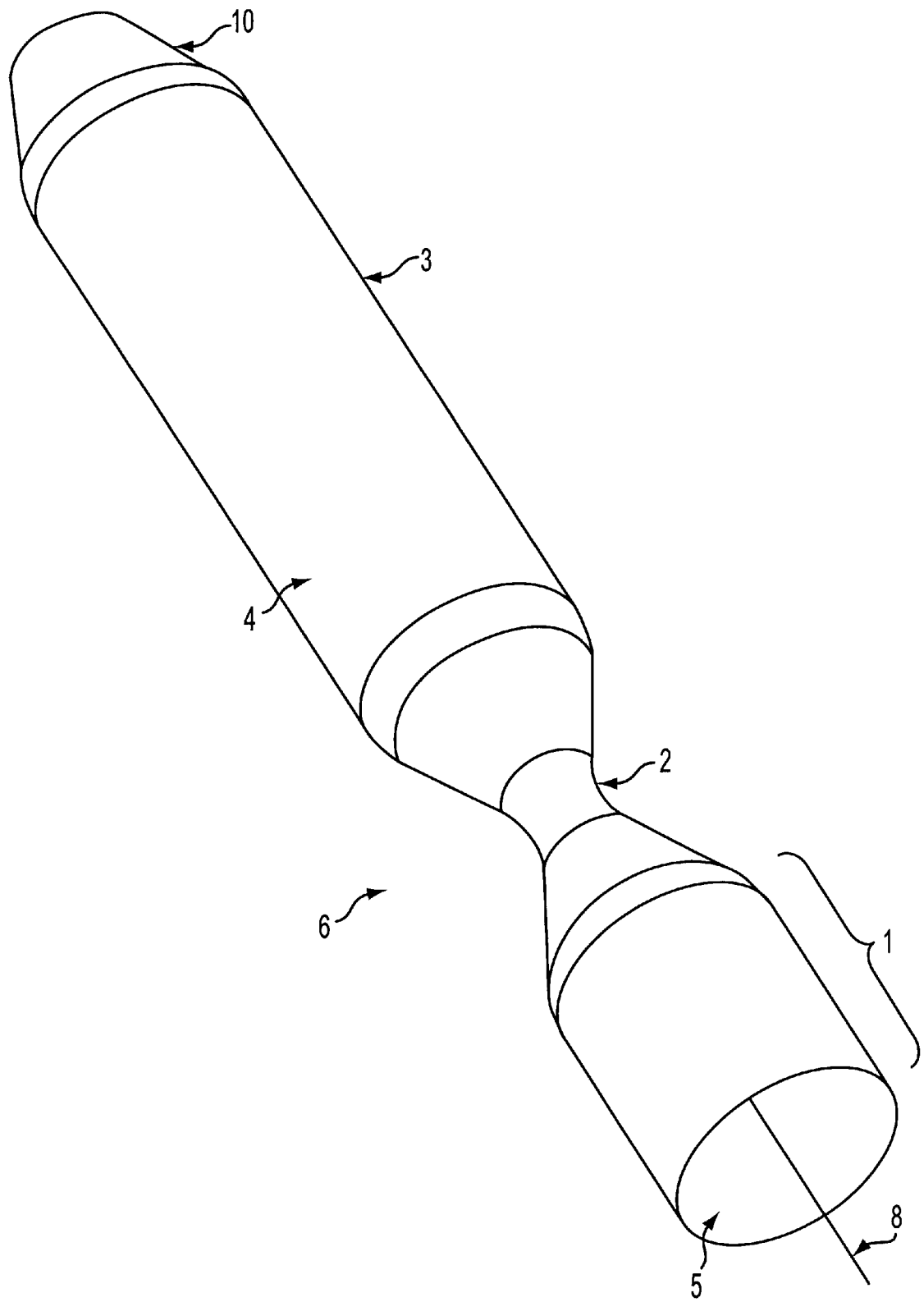
FIG. 3B is a computer-generated drawing showing the high performance cannula according to the invention after removal of the mandrel.
Figure 4:
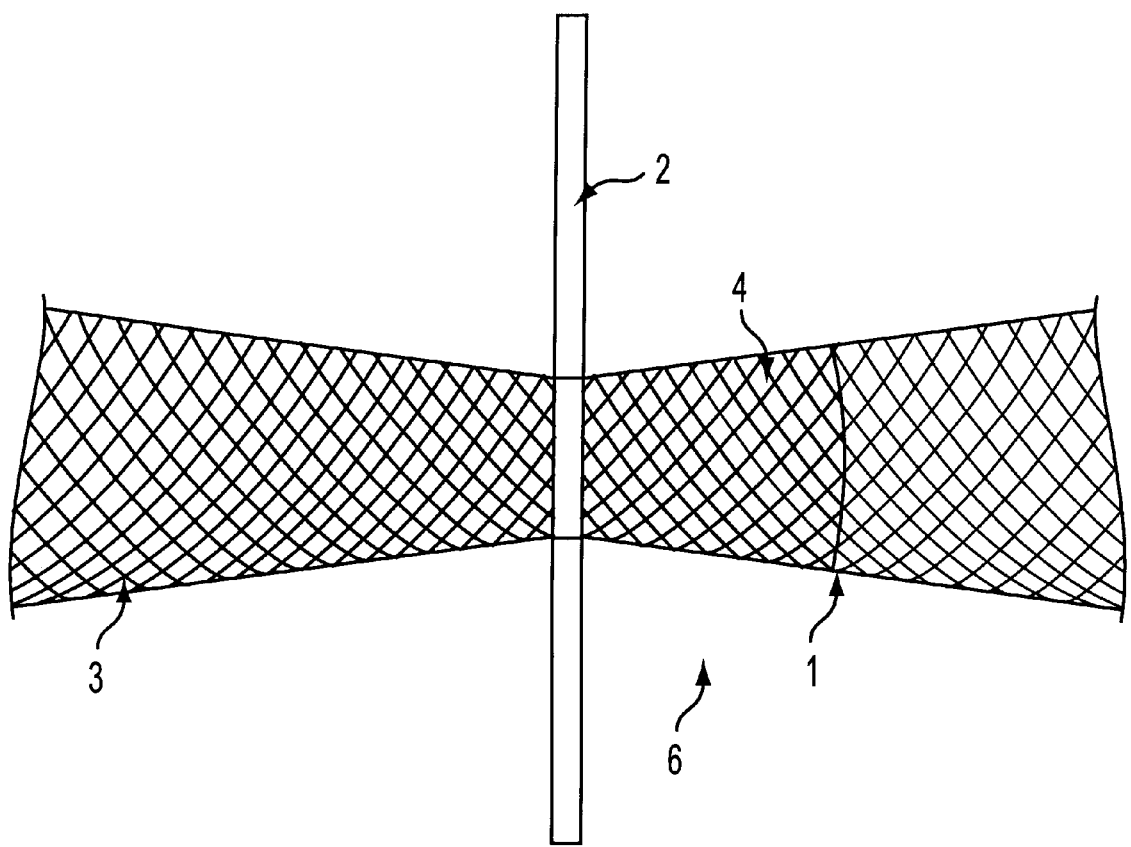
FIG. 4 is a diagram of a prototype high performance cannula according to the invention.

By "normal profile conformation" is meant any conformation similar to that shown in FIG. 2A. According to an embodiment, and as illustrated in FIG. 2A for example, the normal profile conformation may be characterized by the cannula having a lumen diameter at the point of insertion which is smaller than the lumen diameter both proximal and distal to the point of insertion. In its normal profile conformation, the cannula 6 is characterized by a larger diameter of the lumen 5. In the normal profile conformation the cannula 6 has the shape and diameter of the lumen 5 of the cannula 6 prior to cannulation. By "low profile conformation" is meant any conformation similar to that shown in FIG. 2B. According to an embodiment, and as illustrated in FIG. 2B for example, the low profile conformation may be characterized by the cannula having a lumen diameter at the point of insertion that is greater than the lumen diameter distal to the point of insertion. In its low profile conformation, a portion of the cannula 6 is characterized by a narrow diameter of the lumen 5 that is suitable for insertion into the object to be cannulized as well into as smaller access vessels. The low profile conformation of the cannula 6 can be achieved by the deformation of a shape memory metal, the deformation of an elastic, bendable, moldable, or flexible material; activating one or more diameter-varying mechanisms; and deactivating one or more diameter-varying mechanisms. One skilled in the relevant art will also recognize that the low profile conformation can be achieved before, during, and/or after cannulation.

The cannula body 4 may be made out of any flexible material that allows the diameter of the lumen 5 to be varied. The material may be, for example, a plastic, a shape memory metal, or a series of interlaced or interwoven wires. Additionally, the material may also be spring-loaded or torsioned to further allow the diameter of the lumen 5 to be varied. When the material is altered, e.g. stretched, spring-loaded, deformed, activated, compressed, or torsioned, the diameter of the lumen 5 is decreased. The diameter of the lumen 5 returns to its normal profile conformation upon termination of the alteration.

In this embodiment, the diameter of the lumen 5 at the point of insertion 2 is narrower than the diameter at the proximal end 1 and the distal end 3. The diameter of the lumen 5 at the proximal end 1 and the distal end 3 may be the same or different. Typically, the diameter of the lumen 5 at the distal end 3 is greater than the diameter of the lumen 5 at the point of insertion 2. The diameter of the lumen 5 distal to the point of insertion 2 is either the same as the diameter proximal to the point of insertion or it expands to that of the surrounding vessel or environment.

Figure 1C:
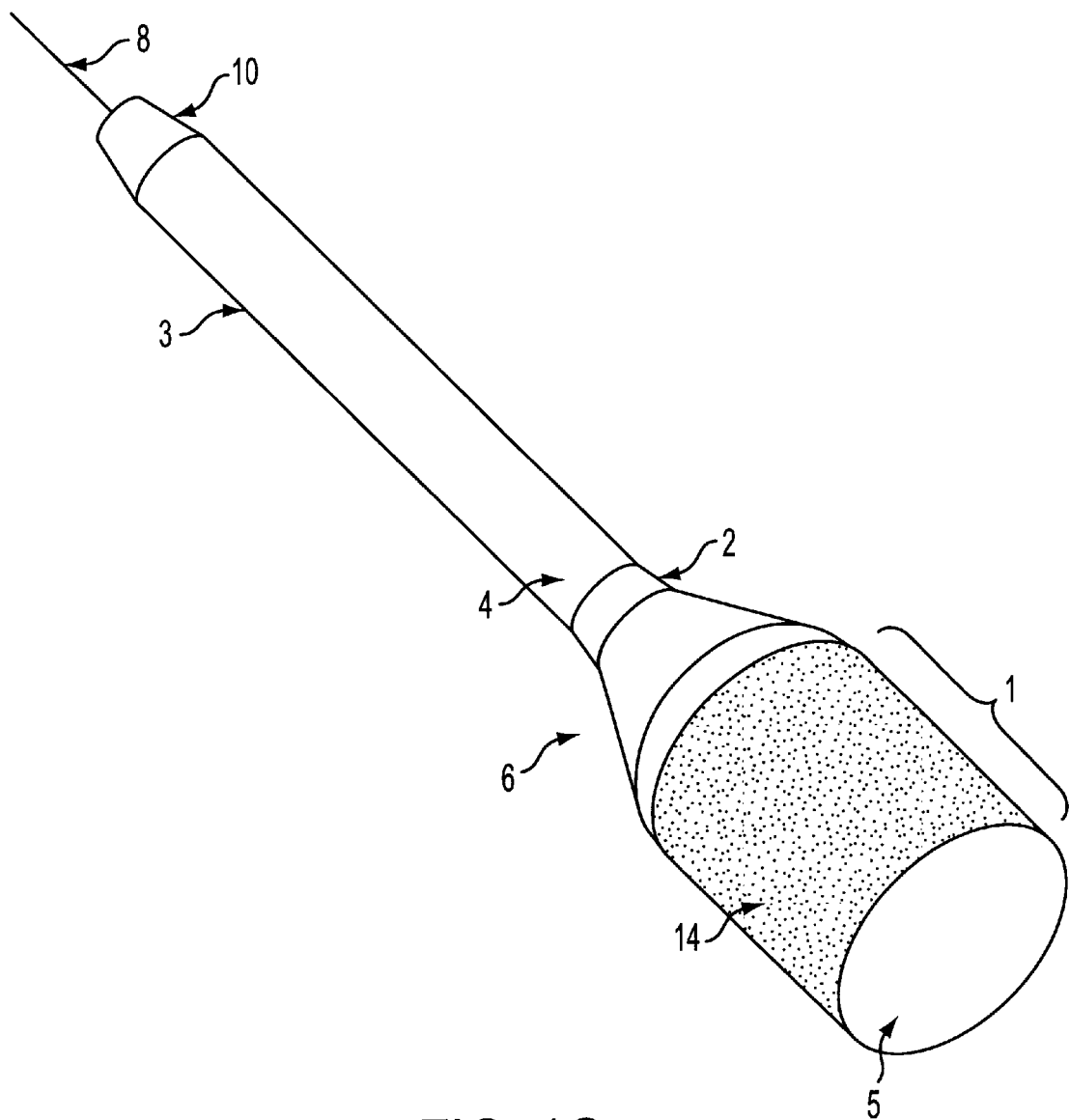
FIG. 1C illustrates a cannula according to an embodiment of the present invention.

Additionally, the material comprising the cannula body 4 may be coated with a water-tight coating. As illustrated in FIG. 1C, a layer 14 of water-tight coating is depicted on the surface of cannula 6. In one embodiment, the water-tight coating is a plastic. However, one skilled in the relevant arts will recognize that any suitable water-tight coating may also be used. In one embodiment, the layer 14 of water-tight coating covers the entire cannula body 4. Alternatively, in a different embodiment, the layer 14 of water-tight coating only covers the proximal end 1 of the cannula body 4.

In another aspect, the invention also comprises a cannula 6 comprising a cannula body 4 having a proximal end 1, a distal end 3, and a lumen 5 having a variable diameter extending between the proximal end 1 and the distal end 3. Ideally, this cannula 6 has a narrow diameter at its point of insertion 2. After insertion, the diameter of the lumen 5 expands distal to the point of insertion 2. In one embodiment, the diameter of the lumen 5 distal to the point of insertion 2 expands to be the same as the diameter of the lumen 5 proximal to the point of insertion 2. Alternatively, the diameter of the lumen 5 distal to the point of insertion 2 expands to be greater than the diameter of the lumen 5 proximal to the point of insertion 2. In another embodiment, the diameter of the lumen 5 distal to the point of insertion 2 is limited to the diameter of the surrounding vessel or environment. Alternatively, the diameter of the lumen may return to its relaxed conformation after insertion. Additionally, in further embodiments, the diameter of the lumen 5 proximal to the point of insertion 2 is greater than the diameter of the lumen 5 at the point of insertion.

In a further aspect, the invention comprises a cannula 6 comprising a cannula body 4 having a proximal end 1, a distal end 3, and a lumen 5 with a diameter extending between the proximal end 1 and the distal end 3. In this respect, the cannula 6 additionally includes one or more mechanisms that allow the diameter of the lumen 5 to be altered. Suitable mechanisms include, but are not limited to, coils; springs; extensible, compressible, or releasable wings; foils; folds; and/or cages. Those skilled in the art will recognize that any mechanism(s) that allows the diameter of the lumen 5 to be varied can also be used.

In one embodiment, the cannula 6 returns to its normal profile conformation upon release of the mechanism(s). In an alternative embodiment, the cannula 6 returns to its normal profile conformation upon activation of the mechanism(s). Alternatively, upon release or activation of the mechanism(s), the diameter of the lumen 5 distal to the point of insertion 2 expands to that of the surrounding vessel or environment.

The diameter of the lumen 5 at the point of insertion 2 is narrower than the diameter of the lumen 5 at both the proximal end 1 and the distal end 3. The diameter of the lumen 5 at the proximal end 1 and the distal end 3 is either the same or different. When the diameter of the lumen 5 at the proximal 1 and distal 3 ends is different, the diameter of the lumen 5 at the proximal end 1 may be either greater than or less than the diameter of the lumen 5 at the distal end 3.

In any of the embodiments, the cannula body 4 may be coated with a water-tight coating. The water-tight coating can be a plastic. However, one skilled in the art will recognize that any suitable water-tight coating may also be used. The water-tight coating may cover the entire cannula 6, or, alternatively, it may cover only the proximal end 1 of the cannula 6.

The cannulas according to the invention are characterized by a high rate of fluid flow through the lumen 5. Specifically, the rate of fluid flow through the lumen 5 is between 1 mL/min and 100 L/min. Preferably, the rate of fluid flow is between 100 mL/min and 6 L/min. When used for heart surgery, typical fluid flow rates through the cannula 6 are on the order of 4–6 L/min. When used for dialysis, typical fluid flow rates through the cannula 6 are on the order of 100 mL/min. The use of the cannulas according to the invention is desirable for any application where a continuous fluid flow is required, and a small access aperture is desired.

The cannulas according to the invention can be a variety of sizes. For example, they can be miniaturized for use in the cannulization of small vessels or objects. Alternatively, they can be enlarged for cannulization of larger vessels or objects.

Method of Using High Performance Cannulas

The invention also comprises methods for using the high performance cannulas according to the invention. In one embodiment, the method involves placing the cannula 6 in its low profile confirmation, inserting the cannula 6 into the object to be cannulized, and returning the cannula 6 to its normal profile conformation. In one embodiment, in the normal profile confirmation, the cannula 6 returns to its original shape and diameter distal to the point of insertion 2. In a different embodiment, in the normal profile conformation, the cannula 6 expands to the internal diameter of the surrounding vessel or environment distal to the point of insertion 2. When used according to these methods, the cannulas of the invention result in a smaller access aperture than other cannulas that are commonly used for cannulization. Advantageously, this smaller access aperture does not adversely impact the flow rate of fluids through the cannula 6.

Alternatively, in a different embodiment, the method comprises activating one or more mechanisms that allow the internal diameter of the lumen 5 of the cannula 6 to be altered; inserting the cannula 6 into the object to be cannulized; and releasing the mechanisms, thereby allowing the cannula 6 to expand distal to the point of insertion 2. In a further embodiment, the method comprises deactivating one or more mechanisms, thereby allowing the internal diameter of the lumen 5 to be decreased, inserting the cannula 6, and reactivating the mechanism to allow the diameter of the lumen 5 to increase. In both embodiments, the diameter of the lumen 5 after the insertion step either expands to that of the surrounding vessel or environment or it returns to its original shape and diameter.

When used according to the methods of the invention, the conformation of the cannula 6 can be altered before, during, and/or after cannulation.

Cannulas according to the instant invention can be used in a variety of medical and non-medical contexts. For example, the methods outlined above can be used for percutaneous insertion, central cannulation, tracheal tubes, chest tubes, drainage catheters, in heart surgery, and dialysis as well as in any non-medical or extramedical situations or applications in which a continuous fluid flow and a small access aperture are desirable. Those of ordinary skill will recognize that the cannulas according to the invention will be suitable for a variety of purposes whenever a minimally invasive means of obtaining a continuous flow of fluids is desired.

Because of the ability to decrease the diameter of the lumen 5 of the cannula 6 at the point of insertion 2 without impacting the flow rate of fluids through the cannulas, the cannulas according to the invention are particularly suitable for use in minimally invasive procedures and/or surgeries. By way of non-limiting example, the cannulas of the invention can be used for blood gas measurement and for establishing a continuous shunt.

The cannulas according to the invention may be included as a part of a high performance cannulation kit. In one embodiment, the kit may include a sharp hollow needle, a J-type guidewire 8, a set of dilators, a mandrel 7 having a locking mechanism 12, and the high performance cannulas of the instant invention packaged together. One skilled in the relevant art will recognize that kits comprising other elements can also be used.

The invention will be further described in the following examples, which do not limit the scope of the invention described in the claims.

EXAMPLE 1

In vivo Cannula Comparisons

In vivo experiments in bovine were conducted to compare the flow rate of fluids through the high performance cannula 6 of the invention and other commercially available cannulas of various diameters. Specifically, the comparisons involved the cannulation of the superior vena cava (the target vessel) through the jugular vein (the access vessel) after calibration of the aperture (through which the cannula and blood flow have to pass) access to 28 French (9.33 mm), 24 French (8 mm), and 20 French (6.66 mm) cannulas. The cannulas tested included DLP cannulas (Medtronic), Biomedicus cannulas (Medtronic), generic chest tube cannulas, and the high performance cannulas according to the instant invention. To insure standardized conditioning, gravity drainage was set at 60 cm of water for each of the cannulas tested.

The results of the comparisons are shown in Table 1.

TABLE 1

| | Comparison A 28 French (9.33 mm) | | | Comparison B 24 French (8 mm) | | | Comparison C 20 French (6.66 mm) | | |
|---|---|---|---|---|---|---|---|---|---|
| | Y | SD | N | Y | SD | N | Y | SD | N |
| DLP cannulas | 4.117 | 0.076 | 3 | 3.317 | 0.076 | 3 | 1.733 | 0.153 | 3 |
| Biomedicus cannulas | 3.983 | 0.046 | 3 | 3.930 | 0.036 | 3 | 2.670 | 0.070 | 3 |
| Chest tube | 3.603 | 0.055 | 3 | 2.947 | 0.117 | 3 | 2.210 | 0.046 | 3 |
| High performance cannulas | 5.350 | 0.132 | 3 | 5.217 | 0.076 | 3 | 4.173 | 0.087 | 3 |

The results depicted in Table 1 demonstrate the flow rate of fluids (Y) in L/min through each of the cannulas tested. The results also show the standard deviation (SD) and number tested (N) for each cannula. For all tested, clinically-relevant cannula diameters (i.e., 28 French, 24 French, and 20 French), the high performance cannulas described herein provided the best flow rate results. The flow rate of fluids through the high performance cannulas was 33–60% higher than the flow rate through the other commonly used, commercially available cannulas. Specifically, for the 20 French outflow vessel, the flow rate with the high performance cannula was superior to the flow rate for the best 28 French cannula (4.117 L/min vs. 4.173 L/min).

Figure 5:
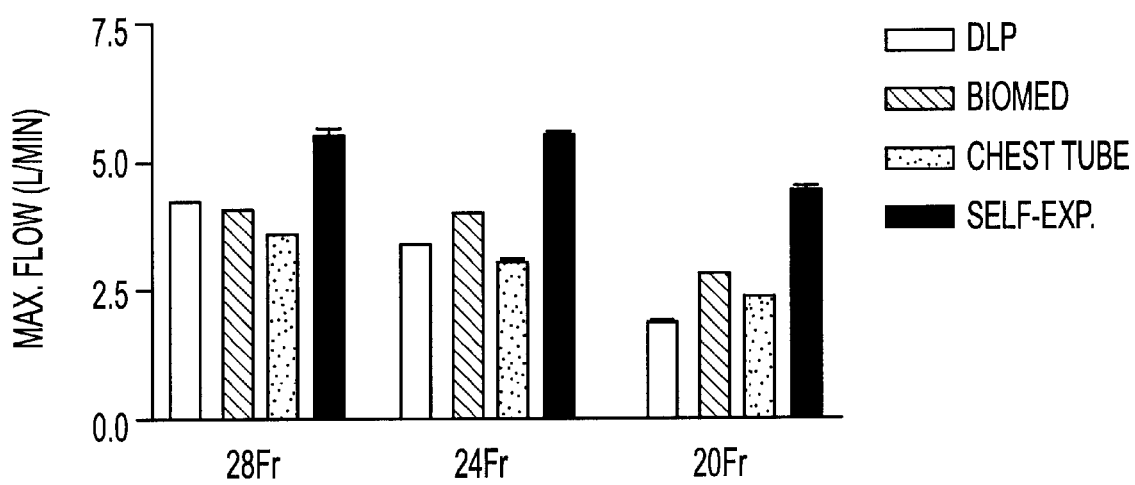
FIG. 5 is a histogram showing the results of in vivo comparison experiments measuring the flow rates through various commercially available cannulas and the high performance cannulas of the instant invention.

Thus, these results demonstrated that the high performance cannulas according to the instant invention are superior to the cannulas commonly used by those skilled in the art. These results provided proof of the principle that the flow rate usually generated with a 28 French cannual can also be provided by a high performance cannula requiring only a 20 French hole. The results of these in vivo comparisons are also shown in FIG. 5.

EXAMPLE 2

Use of High Performance Cannulas

In order to prepare the high performance cannula 6 for use, a mandrel 7 (as shown, for example, in FIG. 3A) is introduced into the cannula 6. Next the cannula 6 is stretched over the mandrel 7 in order to reduce its diameter. Once the cannula 6 is fully in its low profile conformation, it will have a minimal outer diameter.

The vessel to be cannulized is then punctured with the sharp hollow needle. A J-tip guidewire 8 is then introduced into the vessel. Proper positioning of the guidewire is checked by ultrasound, fluoroscopy, or any other suitable means. While keeping the guidewire in place in situ, the needle is then removed from the vessel.

To achieve vessel orifice (i.e., access aperture) dilation, a small (e.g., No. 1) dilator is placed over the guidewire 8 and then removed, while the guidewire 8 remains in place. The access aperture can be redilated using an intermediate (No. 2) dilator that is inserted and removed. Finally, the largest dilator (No. 3) is inserted and removed.

While insuring that the guidewire 8 remains in the proper position, the fully stretched and locked high performance cannula 6 is loaded onto the guidewire 8. This is accomplished by passing the guidewire 8 through the central hole 9 at the tip 10 of the cannula 6 and through the central hole at the tip of the mandrel 7. The cannula 6 is inserted over the wire through the predilated hole in the vessel at the target site.

Once the mandrel 7 is unlocked, the cannula 6 can be pulled back at any time. However, for further advancement, reloading of the cannula 6 onto the mandrel 7 may be necessary. After the mandrel 7 is unlocked, the high performance cannula 6 will expand in situ. Prior to complete removal of the mandrel 7, the position of the cannula 6 should be checked.

If an adequate cannula position is reached, the high performance cannula 6 may be secured and the mandrel 7 removed. Finally, the secured high performance cannula 6 can be connected to a line. A mandrel 7 may be used for repositioning.

EXAMPLE 3

Manufacture of High Performance Cannulas

The manufacture of the high performance cannulas may include some or all of the following steps: (a) defining the diameter and length needed; (b) selecting the appropriate materials; (c) preparing the cannula 6; (d) preparing the mandrel 7; and (e) preparing a locking mechanism 12. Additionally, one of ordinary skill in the relevant arts will recognize that the high performance cannulas of the invention may also be made by any other methods or processes known in the art.

A variety of parameters influence and define the optimal diameter and length configuration of the high performance cannulas of the invention. These parameters include target flow, target vessel diameter, target vessel length, target vessel access diameter, target vessel access length, desired covered cannula 6 length proximal to the point of insertion, and/or the desired connector. In one embodiment the cannula 6 can be approximately ⅜" in diameter and 50–70 cm, depending on the particular application. Determination of the appropriate diameter length is within the routine skill of those in the art.

Suitable materials for manufacturing the high performance cannulas can be categorized as cannula size-independent materials and cannula size-dependent materials. Size-independent materials may include, but are not limited to, medical grade polyurethanes (used for potting the cannula tip 10), medical grade silicones (used for covering the portion of the cannula 6 close to the connector 11), and medical grade plastic separating agents. The cannula lumen 5 may contain a spacer that functions to maintain a hole for the guidewire 8 in the potted cannula tip 10.

Cannula size-dependent materials include the interlaced self-expanding wires that comprise the cannula body 4. Alternatively, an elastic honeycomb structure, a grid, a lasercut nitinol, or a plastic scaffold may be used. The wires can be made of, for example, a medical grade stainless steel coated with a plastic. Other size-dependent materials include molds for potting the cannula tip 10, the connector 11, the mandrel 7, and the locking mechanism 12.

The high performance cannulas 6 of the invention should be made with additional working length at both ends of the final cannula 6 dimensions. The interlaced wire bundle at the distal end 3 of the cannula 6 is tied together to a minimal diameter after the insertion of a central spacer wire, which has been treated with a separate form of the potting material. Any excess length can then be removed.

Using a mold prepared with a separating agent, the cannula tip 10 is positioned within the mold. A polyurethane used for potting is mixed, centrifuged, and potted on the cannula tip 10. Following polymerization and unmolding, the spacer is removed, thereby providing a path for the guidewire 8. Finally, the cannula tip 10 is cut and polished.

Next, the proximal end 1 of the cannula 6 can be coated. Using positioning tools, a partial length dip coating of the proximal end 1 is performed. This dip coating can be a medical grade silicone or any other suitable coating. This coating is then polymerized, and several additional layers can be added. Finally, the proximal end 1 of the cannula 6 can be mounted with an appropriate connector 11.

In order to prepare the mandrel 7, an adequate diameter of Teflon (or any other flexible (i.e., plastic) rod having a conical tip and a central lumen for the guidewire 8, is used. The length of this rod is then adapted for the length of the high performance cannula 6 to be used.

Figure 6A:
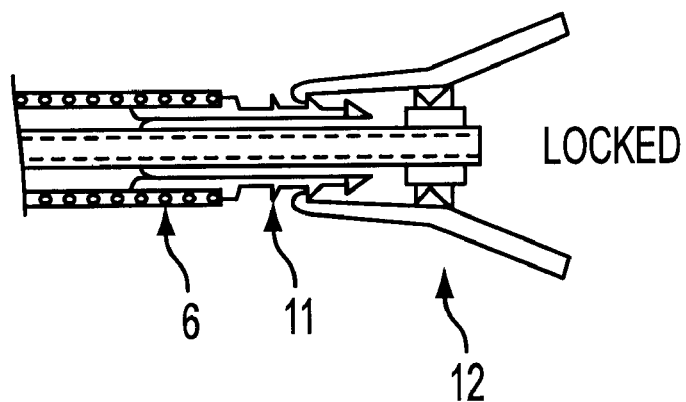
FIGS. 6A–6C illustrate a locking mechanism used with the high performance cannulas of the invention.
Figure 6B:
Figure 6C:
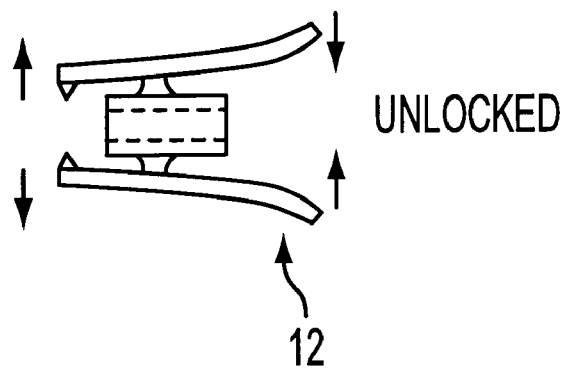

Finally, the locking mechanism 12 is made by selecting an adequate cap with a locking mechanism that is assembled with the cannula 6. Care should be taken to select a locking mechanism 12 of proper length for the selected high performance cannula 6. An example of an appropriate locking mechanism 12 is illustrated in FIGS. 6A–6C.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A cannula adapted for insertion into a patient at a point of insertion, the cannula comprising:

a cannula body having a proximal end, a distal end, and a lumen extending between the proximal and distal ends, the lumen having a diameter, the cannula further comprising a flexible material that allows the diameter of the lumen to be varied;

at least one mechanism that upon actuation serves to alter the conformation of the cannula between a normal profile conformation and a low profile conformation;

wherein the normal profile conformation is characterized by the cannula having a lumen diameter at the point of insertion which is smaller than the lumen diameter both proximal and distal to the point of insertion, and wherein the lumen diameter distal to the point of insertion is expandable to the diameter of a vessel of the patient; and wherein the low profile conformation is characterized by the cannula having a lumen diameter at the point of insertion that is greater than the lumen diameter distal to the point of insertion.

2. The cannula of claim 1 wherein the diameter of the lumen at the proximal and distal ends is the same when in the normal profile conformation.

3. The cannula of claim 1 wherein the diameter of the lumen at the proximal and distal ends is different when in the normal profile conformation.

4. The cannula of claim 1 wherein the diameter of the lumen at the proximal and distal ends is different when in the low profile conformation.

5. The cannula of claim 1 wherein at least the proximal end is coated with a water-tight coating.

6. The cannula of claim 5 wherein the water-tight coating is a plastic.

7. The cannula of claim 1 wherein the cannula is characterized by a high flow rate of fluids through the cannula.

8. The cannula of claim 7 wherein the flow rate of fluids through the cannula is between 100 mL/min and 6 L/min.

9. A method of using the cannula of claim 1, the method comprising:
   a) placing the cannula in its low profile conformation;
   b) inserting the cannula; and
   c) returning the cannula to its normal profile conformation,
   wherein in the normal profile conformation, the cannula expands distal to the point of insertion.

10. The method of claim 9 wherein the cannula is characterized by a high flow rate of fluids through the cannula.

11. The method of claim 10 wherein the flow rate of fluids through the cannula is between 100 mL/min and 6 L/min.

12. A method of using the cannula of claim 1, the method comprising the steps of:
    a) activating the at least one mechanism;
    b) inserting the cannula; and
    c) deactivating the at least one mechanism, thereby allowing the cannula to expand distal to the point of insertion.

13. The method of claim 12 wherein the cannula is characterized by a high flow rate of fluids through the cannula.

14. The method of claim 13 wherein the flow rate of fluids through the cannula is between 100 mL/min and 6 L/min.

15. A cannula adapted for insertion into a patient at a point of insertion, the cannula comprising:
    a cannula body having a proximal end, a distal end, and a lumen extending between the proximal and distal ends, the lumen having a diameter, the cannula further comprising a flexible material that allows the diameter of the lumen to be varied;
    means for altering the conformation of the cannula between a normal profile conformation and a low profile conformation;
    wherein the normal profile conformation is characterized by the cannula having a lumen diameter at the point of insertion which is smaller than the lumen diameter both proximal and distal to the point of insertion, and wherein the lumen diameter distal to the point of insertion is expandable to the diameter of a vessel of the patient; and
    wherein the low profile conformation is characterized by the cannula having a lumen diameter at the point of insertion that is greater than the lumen diameter distal to the point of insertion.

* * * * *